United States Patent [19]
Darsow et al.

[11] Patent Number: 4,684,720
[45] Date of Patent: Aug. 4, 1987

[54] PROCESS FOR THE PREPARATION OF A MIXTURE OF α-D-GLUCOPYRANOSIDO-1,6-MANNITOL AND α-D-GLUCOPYRANOSIDO-1,6-SORBITOL FROM α-D-GLUCOPYRANOSIDO-1,6-FRUCTOSE

[75] Inventors: Gerhard Darsow; Wolfgang Biedermann, both of Krefeld, Fed. Rep. of Germany

[73] Assignee: Bayer Aktiengesellschaft, Leverkusen, Fed. Rep. of Germany

[21] Appl. No.: 692,600

[22] Filed: Jan. 18, 1985

[30] Foreign Application Priority Data

Feb. 4, 1984 [DE] Fed. Rep. of Germany ....... 3403973

[51] Int. Cl.$^4$ .......................................... C07H 15/08
[52] U.S. Cl. .................................... 536/124; 536/125; 568/863; 568/881
[58] Field of Search ................ 536/124, 125; 568/863, 568/881

[56] References Cited

U.S. PATENT DOCUMENTS

| 4,233,439 | 11/1980 | Schiweck et al. | 536/4.1 |
| 4,322,569 | 3/1982 | Chao et al. | 568/863 |
| 4,380,679 | 4/1983 | Arena | 568/863 |
| 4,380,680 | 4/1983 | Arena | 568/863 |
| 4,401,823 | 8/1983 | Arena | 568/863 |

FOREIGN PATENT DOCUMENTS 2520173 12/1976 Fed. Rep. of Germany ....... 536/4.1

*Primary Examiner*—Ronald W. Griffin
*Attorney, Agent, or Firm*—Sprung Horn Kramer & Woods

[57] ABSTRACT

In the preparation of a mixture of α-D-glucopyranosido-1,6-mannitol and α-D-glucopyranoside-1,6-sorbitol by catalytically hydrogenating α-D-glucopyranosido-1,6-fructose in aqueous solution with hydrogen under increased pressure and at elevated temperature, the improvement which comprises effecting the hydrogenation continuously over a fixed bed of support-free shaped pieces of elements of sub-group 8 of the periodic table, which serve as the hydrogenation catalyst. The product can be directly used as a sweetener, without purification. The catalyst life is extremely long.

8 Claims, No Drawings

PROCESS FOR THE PREPARATION OF A MIXTURE OF α-D-GLUCOPYRANOSIDO-1,6-MANNITOL AND α-D-GLUCOPYRANOSIDO-1,6-SORBITOL FROM α-D-GLUCOPYRANOSIDO-1,6-FRUCTOSE

The invention relates to a process for the preparation of a mixture of the diastereomeric sugar-alcohols α-D-glucopyranosido-1,6-mannitol and α-D-glucopyranosido-1,6-sorbitol from α-D-glucopyranosido-1,6-fructose by hydrogenation with hydrogen.

The course of the reaction can be illustrated by the following equation:

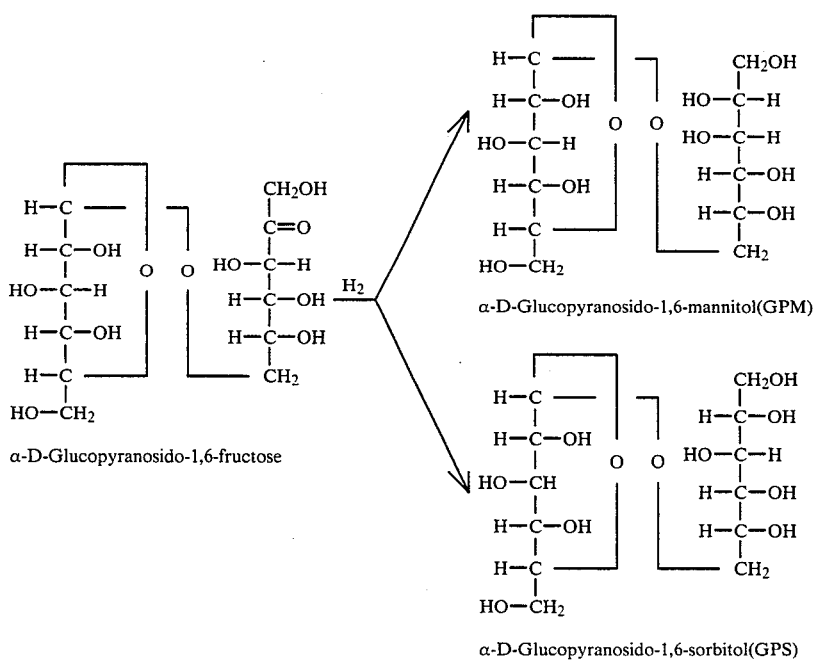

It has been found that mixtures of the sugar-alcohols α-D-glucopyranosido-1,6-mannitol and α-D-glucopyranosido-1,6-sorbitol are obtained in almost quantitative yield if the hydrogenation of the α-D-glucopyranosido-1,6-fructose is carried out continuously under particular reaction conditions over support-free shaped pieces of elements of sub-group 8 of the periodic system, in particular nickel, cobalt and iron, which serve as hydrogenation catalysts. This is of all the more significance, taking into consideration that the removal of high molecular weight or low molecular weight troublesome impurities from the reaction mixture requires a very substantial technical effort if the desired sugar-alcohols are not to be isolated individually from the reaction mixture but are to be obtained in solid form as a sugar-alcohol mixture by concentration of their aqueous solution.

In the known processes for the preparation of α-D-glucopyranosido-1,6-sorbitol (German Patent Specification No. 2,217,628) and α-D-glucopyranosido-1,6-mannitol (DAS (German Published Specification) No. 2,520,173), a pulverulent nickel catalyst is in each case used as the hydrogenation catalyst in a discontinuous suspension process (batch process). Discontinuous processes have the disadvantage that their capacity in relation to the reaction volume is very small and there is therefore a need for large reaction apparatuses and storage tanks. The energy consumption and personnel requirement are relatively high. Continuous powdered catalyst processes which operate with several hydrogenation reactors connected in a cascade avoid some of these disadvantages. However, there is still the need for the pulverulent catalyst to be doped in a controlled manner, circulated by pumping and filtered off quantitatively from the reaction product. The catalyst sludge pumps are subject to a high degree of mechanical wear. Quantitative removal of the pulverulent catalyst from the reaction product is expensive. Furthermore, there is a great danger of reducing the activity of the catalyst relatively rapidly by the additional operations. It is therefore advantageous to allow the reaction to proceed over a catalyst arranged in a fixed bed. Such a catalyst would have to have a high activity, which should not diminish over a prolonged period, because frequent changing of the catalyst is also expensive in the case of fixed bed reactions.

All these disadvantages are overcome by the process according to the invention.

The process according to the invention enables the crystalline mixture of the two diastereomeric sugar-alcohols to be prepared in a purity of more than 99%, the content of unreacted α-D-glucopyranosido-1,6-fructose being less than 0.1% and the sum of sorbitol and mannitol being less than 0.2%. Pure crystalline α-D-glucopyranosido-1,6-fructose is used as the starting compound for the process according to the invention. This substance is prepared from pure sucrose solutions by enzymatic conversion with living or immobilized cell systems by known methods (for example German Patent Specification No. 1,049,800).

The α-D-glucopyranosido-1,6-fructose is dissolved in oxygen-free drinking water, which is purified over active charcoal and an iron filter.

A 45 to 60% strength, preferably 50 to 55% strength, aqueous solution, the pH value of which is adjusted exactly to 3.5–6.5, preferably 5–6.5, is prepared from α-D-glucopyranosido-1,6-fructose and deionized drinking water. When dissolved in water with a pH value of 7, crystalline α-D-glycopyranosido-1,6-fructose gives either a neutral or—as a result of traces of gluconic acid formation possibly caused by a Cannizarro reaction—a weakly acid reaction. Adjustment of the pH to the desired value can be effected, for example, by addition of an organic acid which is as pure as possible. Doping with dilute formic acid, acetic acid, citric acid and sorbic acid has proved particularly suitable.

Pure hydrogen precompressed to a pressure of 100–500 bar, preferably 200–300 bar, is used for the hydrogenation process. The hydrogenation is carried out continuously in a fixed bed process over support-free shaped pieces of a metallic nature, which served as the hydrogenation catalyst, by a procedure in which the solution to be hydrogenated is either allowed to flow in cocurrent with the previously admixed hydrogen over the shaped pieces filling a hydrogenation reactor, from the bottom or top, or is passed in counter-current, from the bottom, with the hydrogen flowing in from the top, or vice versa (counter-current process).

The hydrogenation reactor can be either a single high pressure tube of steel or a steel alloy which is completely or partly filled with the shaped pieces, in which case it may be useful to employ trays (wire baskets and the like), or a jacketed bundle of high pressure tubes, the individual tubes of which are completely or partly filled with the shaped pieces.

The support-free shaped pieces are prepared from metal powders of elements of sub-group 8 of the periodic table, in particular nickel, cobalt and iron, it being possible to use either powders of the pure metals or powdered alloys of the metals. The shaped pieces are prepared by the customary methods, by pressing the metal powders on tabletting or pelleting machines under a high pressure, it also being possible to use small amounts of graphite or to use adhesives, in order to improve the adhesion of the metal particles. The shaped pieces must be prepared in an oxygen-free atmosphere, in order to avoid surface oxidation reactions. Tabletted or pelleted shaped pieces with diameters of 5–10 mm are most effective and are most suitable for the reaction procedure. The compressive strength of the shaped pieces is of considerable importance, and, according to the invention, has values of between 120 and 170 kg/cm$^2$. Lower compressive strengths lead to disintegration of the shaped pieces or erosive abrasion, which would cause metallic contamination of the reaction product. The internal surface area of the shaped pieces is also of considerable importance, and, according to the invention, has values of between 25 and 75 m$^2$/g and is decisive for quantitative conversion of the feed materials.

The hydrogenation process is carried out at a temperature of 70° to 115° C., preferably 80°–110° C. Lower temperatres mean high residence times or the sacrifice of a quantitative conversion of the α-D-glucopyranosido-1,6-fructose. Higher temperatures lead to increased formation of sugar-monoalcohols (sorbitol or mannitol) and to uncontrolled side reactions (caramelization, hydrogenating cracking), which can cause discoloration and lead to the formation of further undesirable by-products. The hourly throughput over the catalyst is between 45 and 60 g of α-D-glucopyranosido-1,6-fructose/liter of catalyst, preferably 50–55 g/liter. If the reaction conditions are exactly maintained, quite unexpectedly high catalyst lives of 12,000 hours or more are achieved, which leads to catalyst consumptions of less than 0.15%, which were hitherto unobtainable in the hydrogenation of α-D-glucopyranosido-1,6-fructose. Apart from the high yields of α-D-glucopyranosido-1,6-mannitol and α-D-glucopyranosido-1,6-sorbitol due to the quantitative conversion, and the purity of the mixture, which does not require further purification procedures, as well as the cost-saving continuous procedure, the chief technical advantages of the process according to the invention thus lie also in the extremely low catalyst consumption.

The hydrogenated aqueous solution which leaves the reactor and contains the two sugar-alcohols α-D-glucopyranosido-1,6-mannitol and α-D-glucopyranosido-1,6-sorbitol in a ratio of about 1:1 is let down, during which the excess hydrogen can be collected and, after compression, can be used again, and is filtered and can thus already be used directly as a sugar substitute mixture in liquid form.

However, the water can also be removed from the solution in a known manner via spray-driers or drying drums or by freeze-drying. As a rule, the colorless, glass-clear solution obtained after the filtration is concentrated to a sugar-alcohol content of about 80% in a falling film evaporator or a similarly operating apparatus and is then made to crystallize completely in a vacuum crystallization apparatus. The crystals can be brought to a uniform particle size by a subsequent grinding process and, if necessary, sieving. Although the product thus obtained is free-flowing and appears completely dry, it has a water of crystallization content of about 5%, which is to be attributed to the fact that, in contrast to α-D-glucopyranosido-1,6-sorbitol, α-D-glucopyranosido-1,6-mannitol crystallizes with a water of crystallization content of 10%.

The product obtained starts to melt at 90° C. A clear melt is formed at 140° C. The exact melting range of the anhydrous substance mixture is obtained, for example, by fusing the water-containing product at 110° C. under 10 mbar in a drying apparatus which can be evacuated and allowing the water to evaporate off quantitatively from the melt. A recrystallized sample treated in this manner has a melting range of 138°–143° C.

The solution properties in water of the 1:1 mixture of α-D-glucopyranosido-1,6-mannitol and α-D-glucopyranosido-1,6-sorbitol in the temperature range from 0°–70° C. are between those of the pure substances. At temperatures above 70° C., the solubility of the mixture exceeds that of the pure substances (see the solubility diagram), which appears to be particularly advantageous when the mixture is used as a sweetener for drinks and foodstuffs, especially if the substances in question are to be highly sugared. Both the individual compounds and the mixture exhibit a sweetening power which corresponds to approximately 45% of the sweetening power of sucrose. To increase the sweetening power of the mixture of α-D-glucopyranosido-1,6-mannitol and α-D-glucopyranosido-1,6-sorbitol, artificial sweetener, for examiple cyclohexyl sulphamate or methyl phenylalanine-aspartate, can be added to the aqueous solution and a crystalline form can be obtained by joint vacuum crystallization. However, it is also possible to mix the artificial sweeteners with the crystals in solid form. The mixture of α-D-glucopyranosido-1,6-mannitol and α-D-glucopyranosido-1,6-sorbitol can also be mixed in the liquid or solid form with other sweet-tasting carbohydrates, for example fructose, sorbitol or xylitol.

Like the individual substances, the mixture of α-D-glucopyranosido-1,6-mannitol and α-D-glucopyranosido-1,6-sorbitol is not usually fermented by yeasts. It is also not split by commercially available invertase products or glucosidases. Also like the individual substances, the mixture can therefore also be used as a sweet-tasting, low calorie, structure- and body-forming filler with no unpleasant taste or smack in foodstuffs and luxury items and in drinks, which are also suitable for diabetics and less cariogenic than comparable products produced with sugar.

EXAMPLE 1

A vertical, heat-insulated high pressure tube of stainless steel with an internal diameter of 45 mm and 1 m in length is filled with 1.4 liters of a hydrogenation catalyst which is prepared by tabletting nickel powder and has a cylinder height of 5 mm, a diameter of 5 mm, a compressive strength of 147 kp/cm$^2$ and an internal surface area of 43 m$^2$/g. 140 ml per hour of a 50% strength solution of α-D-glucopyranosido-1,6-fructose in deionized oxygen-free drinking water, which has been brought to a pH value of 6.0, are pumped continuously through this tube, together with three times the molar amount of highly pure hydrogen under a pressure of 300 bar, the substances being pumped in from the bottom upwards.

The aqueous solution and hydrogen are passed through a heat exchanger and are heated so that they enter the high pressure tube with a temperature of 80° C. The mixture of aqueous solution and excess hydrogen which leaves the high pressure tube is passed over a cooler into a separator, from where the hydrogen, after replacement of the amount consumed, is pumped again into the prewarmer together with still unhydrogenated solution, and from there is pumped again into the high pressure tube.

The clear aqueous solution is let down, filtered over a fine filter, concentrated to a sugar-alcohol content of about 80% in a falling film evaporator and then made to crystallise completely in a vacuum crystallizer. The resulting fine crystalline powder consists of a mixture of α-D-glucopyranosido-1,6-mannitol and α-D-glucopyranosido-1,6-sorbitol in a ratio of about 1:1 in the dry matter. The water content is 5%. The mixture of the two stereoisomeric sugar-alcohols is otherwise highly pure (degree of purity ≧99.6%). The content of non-hydrogenated α-D-glucopyranosido-1,6-fructose is ≦0.1%. The content of sorbitol is ≦0.1%. It was not possible to detect mannitol. The activity of the catalyst was unchanged, even after a running time of 12,000 hours. This corresponds to a catalyst consumption of <0.15%/kg of hydrogenated substance.

EXAMPLE 2

As described in Example 1, an equivalent amount per hour of a 50% strength aqueous solution of α-D-glucopyranosido-1,6-fructose which has a pH value of 5.0 is hydrogenated through a high pressure tube, as in Example 1, at a temperature of 110° C. under a hydrogen pressure of 200 bar in reverse reaction flow. The catalyst was prepared by tabletting nickel powder. The tablets have a cylinder height of 5 mm, a diameter of 5 mm, a compressive strength of 143 kp/cm$^2$ and an internal surface area of 69 m$^2$/g.

After a running time of 12,000 hours with no loss in activity, the content of α-D-glucopyranosido-1,6-mannitol and α-D-glucopyranosido-1,6-sorbitol in the reaction mixture evaporated to dryness in a rotary evaporator is 99.3%. The content of non-hydrogenated α-D-glucopyranosido-1,6-fructose is 0.2%. The content of sorbitol is 0.1%. The content of mannitol is 0.01%.

EXAMPLE 3

In the same manner as in Example 1, an equivalent amount per hour of a 50% strength aqueous solution of α-D-glucopyranosido-1,6-fructose which has a pH value of 5.5 is hydrogenated in a high pressure tube, as in Example 1, at a temperature of 115° C. under a hydrogen pressure of 300 bar. The catalyst was obtained by tabletting a a powdered nickel/iron alloy. The alloy has an iron content in the nickel of 15%. The tablets have a cylinder height of 5 mm, a diameter of 5 mm, a compressive strength of 138 kg/cm$^2$ and an internal surface area of 63 m$^2$/g. The 1:1 mixture of α-D-glucopyranosido-1,6-mannitol and α-D-glucopyranosido-1,6-sorbitol obtained in a vacuum crystallizer has a degree of purity of 99.3%. The content of unreacted α-D-glucopyranosido-1,6-fructose is 0.1%. The sorbitol content is 0.1%. The mannitol content is 0.01%. The activity of the catalyst was still unchanged after a running time of 8,000 hours.

EXAMPLE 4

In the same manner as in Example 1, an equivalent amount of a 50% strength aqueous solution of α-D-glucopyranosido-1,6-fructose which has a pH value of 6.0 is hydrogenated in a high pressure tube, as in Example 1, at a temperature of 105° C. under a hydrogen pressure of 200 bar. The catalyst was obtained by tabletting a powdered nickel/cobalt alloy. The alloy has a cobalt content in the nickel of 10%. The tablets have a cylinder height of 5 mm, a diameter of 5 mm, a compressive strength of 137 kg/cm$^2$ and an internal surface area of 29 m$^2$/g. The mixture of α-D-glucopyranosido-1,6-mannitol and α-D-glucopyranosido-1,6-sorbitol obtained in a vacuum rotary tube has a degree of purity of 99.2%. The content of unreacted α-D-glucopyranosido-1,6-fructose is 0.3%. The sorbitol content is 0.15%. No mannitol can be detected. There was still no change in the activity of the catalyst after a running time of 1,000 hours.

EXAMPLE 5

(Comparison Example)

In the same manner as in Example 1, an equivalent amount of a 50% strength aqueous solution of α-D-glucopyranosido-1,6-fructose which has a pH value of 6.0 is hydrogenated in the same time through a high pressure tube, as in Example 1, at a temperature of 100° C. under a hydrogen pressure of 300 bar. The catalyst was prepared by applying an aqueous nickel salt solution to an inert spherical Al$_2$O$_3$ support (bead diameter: 5 mm) and subsequently converting the nickel into the metallic state by reduction in a stream of hydrogen. The nickel content of the catalyst is 18%. The internal surface area of the catalyst is 75 m$^2$/g and thus corresponds to the surface area of the support-free catalysts described above. The 1:1 mixture of α-D-glucopyranosido-1,6-mannitol and α-D-glucopyranosido-1,6-sorbitol obtained in a vacuum crystallizer has a degree of purity of 91.9%. The content of unreacted α-D-glucopyranosido-1,6-fructose is 1.7%. The sorbitol and mannitol content is 0.3%. Unknown impurities were also detected in an amount of 6.1%, so that the mixture of α-D-glucopyranosido-1,6-mannitol and α-D-glucopyranosido-1,6-sorbitol thus obtained in this preparation form cannot be used as a sugar substitute. Furthermore, a reduction in the activity of the catalyst was already observed after a running time of 600 hours. Although it was possible to reduce the content of unreacted α-D-glucopyranosido-1,6-fructose to a value of 0.5% by increasing the reaction temperature from 100° to 120° C., at the same time the content of unknown impurities rose to a value of 6.4%.

EXAMPLE 6

(Comparison Example)

In the same manner as in Example 1, an equivalent amount per hour of a 50% strength aqueous solution of α-D-glucopyranosido-1,6-fructose which has a pH value of 6.0 is hydrogenated through a high pressure tube, as in Example 1, at a temperature of 100° C. under a hydrogen pressure of 300 bar. The catalyst was prepared by applying aqueous nickel salt and iron salt solutions to an inert, spherical $Al_2O_3$ support (bead diameter: 5 mm) and subsequently converting the nickel and iron into the metallic state by reduction in a stream of hydrogen. The nickel content of the catalyst is 16% and the iron content is 4%. The internal surface area of the catalyst is 75 m$^2$/g. The 1:1 mixture of α-D-glucopyranosido-1,6-mannitol and α-D-glucopyranosido-1,6-sorbitol obtained by evaporation in a vacuum crystallizer has a degree of purity of 93.2%. The content of unreacted α-D-glucopyranosido-1,6-fructose is 1.5%. The sorbitol and mannitol content is 0.2%. Unknown impurities were also detected in an amount of 5.1%, so that the mixture of α-D-glucopyranosido-1,6-mannitol and α-D-glucopyranosido-1,6-sorbitol thus obtained cannot be used directly as a sugar substitute. A considerable decrease in catalyst activity was already detected after a running time of 800 hours. The catalyst consumption was >1.5%/kg of hydrogenated substance.

It is understood that the specification and examples are illustrative but not limitative of the present invention and that other embodiments within the spirit and scope of the invention will suggest themselves to those skilled in the art.

We claim:

1. In the preparation of a mixture of α-D-glucopyranosido-1,6-mannitol and α-D-glucopyranoside-1,6-sorbitol by catalytically hydrogenating α-D-glucopyranosido-1,6-fructose in aqueous solution with hydrogen under increased pressure and at elevated temperature, the improvements which comprises effecting the hydrogenation continuously over a fixed bed of support-free shaped pieces of elements of sub-group 8 of the periodic table, which serve as the hydrogenation catalyst.

2. A process according to claim 1, wherein the support-free shaped pieces which serve as the hydrogenation catalyst are shaped pieces prepared from metal powders of nickel, cobalt or iron.

3. A process according to claim 1, wherein the support-free shaped pieces which serve as the hydrogenation catalyst are shaped pieces prepared from powders of the pure metals or from alloys of these metals.

4. A process according to claim 1, wherein the support-free shaped pieces which serve as the hydrogenation catalyst are tabletted or pelleted shaped pieces which are prepared from metal powders and have diameters of about 5–10 mm and a compressive strength of about 120–170 kp/cm$^2$, at an internal surface area of about 25–75 m$^2$/g.

5. A process according to claim 1, wherein the hydrogenation of the α-D-glucopyranosido-1,6-fructose is carried out in about 45 to 60% aqueous solution at a pH of about 3.5–6.5.

6. A process according to claim 1, wherein the hydrogenation of the α-D-glucopyranosido-1,6-fructose is carried out under a hydrogen pressure of about 100 to 500 bar.

7. A process according to claim 1, wherein the hydrogenation of the α-D-glucopyranosido-1,6-fructose is carried out at a temperature of about 70°–115° C.

8. A process according to claim 4, wherein the hydrogenation of the α-D-glucopyranosido-1,6-fructose is carried out in about 50 to 55% aqueous solution at a pH of about 5 to 6.5, under a hydrogen pressure of about 200 to 300 bar and a temperature of about 80° to 110° C.

* * * * *